United States Patent [19]

Patt

[11] Patent Number: 4,764,506

[45] Date of Patent: Aug. 16, 1988

[54] N6-(BENZOTHIEN-3-YL)ETHYL ADENOSINE; N6-(BENZOTHIEN-3-YL)ETHYL ADENOSINE, S-OXIDE; AND N6-(BENZOTHIEN-3-YL)ETHYL S,S-DIOXIDE ADENOSINE

[75] Inventor: William Patt, Chelsea, Mich.

[73] Assignee: Warner-Lambert Company, Morris Plains, N.J.

[21] Appl. No.: 853,536

[22] Filed: Apr. 18, 1986

Related U.S. Application Data

[62] Division of Ser. No. 695,022, Jan. 25, 1985, Pat. No. 4,600,707.

[51] Int. Cl.$^4$ .................................. A61K 31/70
[52] U.S. Cl. ..................... 514/46; 514/45; 514/49; 514/50; 536/24; 536/26
[58] Field of Search .................. 514/46; 536/26

[56] References Cited

U.S. PATENT DOCUMENTS 3,887,706  6/1975  Vorbrüggen .
3,983,104  9/1976  Vorbruggen ................ 536/24
4,636,493  1/1987  Patt ........................... 514/46

OTHER PUBLICATIONS

"Anti-Inflammatory and Immunosuppressive Properties of N6-[3-Chlorbuten-(2)-yl]-Adenosin", A. S. Bhargava and T. Diamanstein; 1974.

Primary Examiner—J. R. Brown
Assistant Examiner—L. Eric Crane
Attorney, Agent, or Firm—Joan Thierstein

[57] ABSTRACT

Benzothien-3-yl adenosine; benzothien-3-yl adenosine, S-oxide; and benzothien-3-yl adenosine, S,S-dioxide compounds or pharmaceutically acceptable acid addition salts having highly desirable central nervous system and antihypertensive properties, processes for their manufacture and pharmaceutical compositions and methods for using said compounds and compositions are described.

12 Claims, No Drawings

N⁶-(BENZOTHIEN-3-YL)ETHYL ADENOSINE; N⁶-(BENZOTHIEN-3-YL)ETHYL ADENOSINE, S-OXIDE; AND N⁶-(BENZOTHIEN-3-YL)ETHYL S,S-DIOXIDE ADENOSINE

This is a division of application Ser No. 695,022 filed Jan. 25, 1985, now U.S. Pat. No. 4,600,707.

BACKGROUND OF THE INVENTION

Various adenosine derivatives are claimed having desirable ratio of affinities at A1 or A2 receptors and highly desirable central nervous system and cardiovascular activities, such as analgesic, antipsychotic, sedative, or antihypertensive, as well as immunoinflammatory activity in copending applications. However, in each case the substituents do not teach the benzothien-3-yl; benzothien-3-yl, S-oxide; and benzothien-3-yl, S,S-dioxide adenosines of the present invention. For example, U.S. Ser. No. 665,219, now U.S. Pat. No. 4,593,019 discloses N⁶-tricyclic adenosines, U.S. Ser. No. 771,591 now U.S. Pat. No. 4,614,732 which is a continuation in part of U.S. Ser. No. 665,195, now abandoned discloses N⁶-acenaphthyl adenosines, U.S. Ser. No. 772,984 which is a continuation in part of U.S. Ser. No. 665,197, now abandoned discloses N⁶-benzopyrano- and benzothiopyrano adenosines, U.S. Ser. No. 771,590 which is a continuation in part of U.S. Ser. No. 665,218, now abandoned discloses N⁶-tetrahydronaphthyl adenosines, U.S. Ser No. 772,983 which is a continuation in part of U.S. Ser. No. 665,216, now abandoned discloses N⁶-bicyclo[2.2.1.]heptyl adenosines, U.S. Ser. No. 771,589 now U.S. Pat. No. 4,616,003 which is a continuation in part of U.S. Ser. No. 665,229, now abandoned discloses N⁶-dihydroxypropyl adenosines, U.S. Ser. No. 665,230 now U.S. Pat. No. 4,626,526 discloses (s)-N⁶-2-hydroxypropyl adenosines, U.S. Ser. No. 772,315 which is a continuation in part of U.S. Ser. No. 665,217, now abandoned discloses N⁶-substituted deoxyribose adenosines, a continuation in part of U.S. Ser. No. 665,233, now abandoned discloses N⁶-substituted-5'-deoxy-5'-chloro adenosines, and a continuation in part also of U.S. Ser. No. 665,232 now abandoned discloses N⁶-substituted-5'-deoxy-5'-methylthioadenosines and, finally U.S. Ser. No. 558,144, now U.S. Pat. No. 4,501,735 discloses benzocycloalkyl adenosines.

Additionally, British No. 1,529,721 discloses an N⁶-substituted adenosine containing the N⁶ nitrogen in a heterocyclic substituent for use as antiproliferative and coronary-circulation-active agents and French No. 6650M (Derwent No. 37,912) discloses N⁶-alkyl, -aryl, -araalkyl, -furfuryl, and -thienyl adenosine compounds for use as antiinflammatory agents.

Finally, a German Offenlegungsschrift No. 2,139,107 discloses adenosine derivatives for increased coronary flow and/or increased oxygen partial pressure in coronary venous blood and circulatory, antilipolytic, and/or hypocholesterolaemic activity. These derivatives disclose N⁶-substituents of adenosine including an R'—(CH$_2$)$_n$—NH-substituent wherein R' may include a benzothienyl group and n is 0, 1, 2, 3, or 4, but, preferably 0 or 1. Substitutions of R' groups are suggested generically but are limited to alkyls or groups attached through alkyls. The only species exemplified having a benzothienyl group has a 3-aminomethylbenzothiophen substituent. Thus, the invention of the present disclosure is either outside the disclosure of the German reference, or provides novel compounds with activity which is not obvious from the disclosure of the reference, for example, for compounds of the present invention having in every case a —CH$_2$CH$_2$ linkage between the benzothienyl group and adenosine residue.

The compounds of the instant invention are adenosine analogs having some of the same activity as adenosine, but having a significantly longer duration of action. A distinguishing feature of these compounds from other adenosine analogs previously described, is the discovery that benzothien-3-yl adenosine; benzothien-3-yl adenosine, S-oxide; and benzothien-3-yl adenosine, S,S-dioxide compounds of the present invention have favourable ratio of affinities at A1 and A2 receptors and highly desirable central nervous system and cardiovascular activities, such as analgesic, antipsychotic, sedative, or antihypertensive. In addition, these adenosine compounds also have immunoinflammatory activity.

SUMMARY OF THE INVENTION

Accordingly the present invention relates to a compound of the formula I wherein n is 0 through 2 ------, is →, or ▬▬▬, X and Y are each independently H, hydroxy, lower alkoxy, lower alkyl, amino, mono-lower alkylamino, di-lower alkylamino, nitro, or halogen; R$_2$ is H, halogen or amino, R$_2'$, R$_3'$, and R$_5'$ are each independently H, lower alkanoyl, benzoyl, or benzoyl substituted by lower alkyl, lower alkoxy, halogen, or when taken together, R$_2'$ and R$_3'$ may be 2', 3'-lower alkylidene, such as isopropylidene; or pharmaceutically acceptable acid addition salts thereof.

The present invention also relates to a pharmaceutical composition comprising a therapeutically effective amount of a compound of the above formula I with a pharmaceutically acceptable carrier, and to a method of treating mammals, including humans, by administering to such mammals a dosage form of a compound of the formula I as defined above.

DETAILED DESCRIPTION

In the compounds of the formula I, the term "lower alkyl" is meant to include a straight or branched alkyl group having from one to six carbon atoms such as, for example, methyl, ethyl, propyl, isopropyl, butyl, sec-butyl, isobutyl, tert-butyl, amyl, isoamyl, neopentyl, hexyl, and the like.

Halogen includes particularly fluorine, trifluoromethyl, chlorine, or bromine.

Lower alkoxy is 0-alkyl of from one to six carbon atoms as defined above for "lower alkyl."

Lower alkanoyl is a straight or branched C(O)alkyl group of from one to six carbon atoms in the alkyl chain as defined above.

The compounds of formula I are useful in the free base form and in the form of acid addition salts. Both forms are within the scope of the invention. In practice, use of the salt form amounts to use of the base form. Appropriate pharmaceutically acceptable salts within the scope of the invention are those derived from mineral acids such as hydrochloric acid and sulfuric acid; and organic acids such as ethanesulfonic acid, benzenesulfonic acid, p-toluenesulfonic acid, and the like, giving the hydrochloride, sulfamate, ethanesulfonate, benzenesulfonate, p-toluenesulfonate, and the like, respectively.

The acid addition salts of said basic compounds are prepared either by dissolving the free base in aqueous or aqueous alcohol solution or other suitable solvents containing the appropriate acid and isolating the salt by evaporating the solution, or by reacting the free base and acid in an organic solvent, in which case the salt separates directly or can be obtained by concentration of the solution.

The compounds of the invention may contain asymmetric carbon atoms. The invention includes the individual diastereomers and mixtures thereof. The individual diastereomers may be prepared or isolated by methods known in the art.

A preferred embodiment is a compound of formula I where one of X and Y is hydrogen, or lower alkyl, and n, $R_2$, $R_2'$, $R_3'$, and $R_5'$ are as defined above.

Another preferred embodiment is a compound of formula I where one of X and Y is not hydrogen or lower alkyl, $n=0$, and $R_2'$, $R_3'$, and $R_5'$ are as defined above.

Another preferred embodiment is a compound of formula I where n is one or two and X, Y, $R_2$, $R_2'$, $R_3'$, and $R_5'$ are as defined above.

Still another preferred embodiment is a compound of formula I where one of X and Y is not hydrogen or lower alkyl and $R_2$ is not hydrogen, and $R_2'$, $R_3'$, and $R_5'$ are as defined above.

A further preferred embodiment is a compound of formula I, wherein one of X and Y is not hydrogen or lower alkyl, $R_2'$, $R_3'$, and $R_5'$ are hydrogen.

A particular preferred embodiment includes $N^6$-2-[3-(5-methylbenzothiophenyl)]ethyl adenosine or a pharmaceutically acceptable salt thereof.

The compounds of formula I may be conveniently synthesized by reacting a 6-halopurine riboside of formula V with the requisite amine corresponding to formula II, III, or IV in an inert solvent such as alcohol, or an aprotic solvent such as dimethylformamide between about 25° to about 130° C. for from 1–48 hours. It is useful to add a base such as triethylamine, or calcium carbonate to neutralize the hydrogen halide formed as a byproduct of the reaction, but this can also be accomplished by using an extra equivalent of the amine. It is also convenient, although not necessary, to protect the ribofuranose hydroxyl groups as acetate or benzoate esters which can be removed with ammonium hydroxide or sodium methoxide following the synthesis of the $N^6$-substituted adenosine. The reaction is illustrated in Scheme I showing the compound V wherein Hal is halogen, preferably chlorine or bromine, and $R_2$, $R_2'$, $R_3'$, and $R_5'$ are as defined above for formula I and the compounds II, III, and IV wherein X and Y are as defined above for formula I.

Compounds of formula I wherein n is one or two can be prepared from the compounds of formula I wherein n is zero by methods known in the art, for example, by oxidation.

The requisite amine starting materials or materials from which the amines can be prepared are available commercially or are prepared using methods known in the literature, for example, J. Heterocycl. Chem., 16(7) 1321–4 (1979), J. Chem. Soc. C, (12), 1612–16 (1969), J. Chem. Soc. C, (12) 1612–16 (1969), J. Org. Chem., 33, 1556–59, (1968).

The compounds of formula I have been found to possess differing affinities for adenosine receptors (designated $A_1$ and $A_2$ receptors for convenience). These compounds are active in animal tests which are predictive of neuroleptic activity for the treatment of major psychoses such as schizophrenia. The compounds of the invention also have sedative/hypnotic properties and as such, are useful for the treatment of sleep disorders.

These compounds also have analgesic properties and as such, are useful in the treatment of pain.

In addition, the compounds of the present invention are useful as antihypertensive agents for the treatment of high blood pressure.

PHARMACOLOGICAL EVALUATION

Adenosine Receptor Binding—$A_1$ Receptor Affinity (RBA1)

Preparation of Membranes

Whole brain minus cerebellum and brainstem from male Long Evans rats (150–200 g) was homogenized in 30 volumes of ice-cold 0.05 M Tris-HCl buffer pH 7.7 using a Brinkman Polytron PT-10, (setting number 6 for 20 seconds) and centrifuged for ten minutes at $20,000 \times g$ (Sorvall RC-2), 4° C. The supernatant was discarded, and the pellet was resuspended and centrifuged as before. The pellet was resuspended in 20 ml Tris-HCl buffer containing two International Units/ml of adenosine deaminase (Sigma type III from calf intestinal mucosa), incubated at 37° C. for 30 minutes, then subsequently at 0° C. for ten minutes. The homogenate was again centrifuged, and the final pellet was resuspended in ice-cold 0.05 M Tris-HCl buffer pH 7.7 to a concentration of 20 mg/ml original wet tissue weight and used immediately.

Assay Conditions

Tissue homogenate (10 mg/ml) was incubated in 0.05 M Tris-HCl buffer pH 7.7 containing 1.0 nM [$^3$H]-$N^6$-cyclohexyladenosine ([$^3$H]-CHA) with or without test agents in triplicate for one hour at 25° C. Incubation volume was 2 ml. Unbound [$^3$H]-CHA was separated by rapid filtration under reduced pressure through Whatman glass fiber (GF/B) filters. The filters were rinsed three times with 5 ml of ice cold 0.05 M Tris-HCl buffer pH 7.7. The radio-labeled ligand retained on the filter was measured by liquid scintillation spectrophotometry after shaking the filters for one hour or longer on a mechanical shaker in 10 ml of Beckman Ready-Solv HP scintillation cocktail.

Calculations

Nonspecific binding was defined as the binding which occurred in the presence of 1 mM theophylline. The concentration of test agent which inhibited 50% of the specific binding (IC$_{50}$) was determined by nonlinear computer curve fit. The Scatchard plot was calculated by linear regression of the line obtained by plotting the amount of radioligand bound (pmoles/gram of tissue)

versus $\left[ \dfrac{\text{bound radioligand}}{\text{free radioligand}} \right]$.

Since the amount of radioligand bound was a small fraction of the total amount added, free radioligand was defined as the concentration (nM) of radioligand added to the incubation mixture. The Hill coefficient was calculated by linear regression of the line obtained by plotting the log of the bound radioligand vs the log of the $$\left[\frac{\text{bound radioligand}}{B_{max} - \text{bound radioligand}}\right]$$

The maximal number of binding sites ($B_{max}$) was calculated from the Scatchard plot.

Adenosine Receptor Binding—$A_2$ Receptor Affinity (RBA2)

Tissue Preparation

Brains from 200–500 g mixed sex Sprague-Dawley rats were purchased from Pel-Freez (Rogers, Ark.). Fresh brains from male Long-Evans hooded rats (Blue Spruce Farms, Altamont, N.Y.) gave essentially identical results. Brains were thawed and then kept on ice while the striata were dissected out. Striata were disrupted in 10 vol of ice-cold 50 mM Tris.HCl (pH 7.7 at 25° C., pH 8.26 at 5° C.) (Tris) for 30 seconds in a Polytron PT-10 (Brinkmann) at setting 5. The suspension was centrifuged at 50,000 xg for ten minutes, the supernatant discarded, the pellet resuspended in 10 vol ice-cold Tris as above, recentrifuged, resuspended at 1 g/5 ml, and stored in plastic vials at $-70°$ C. (stable for at least six months). When needed, tissue was thawed at room temperature, disrupted in a Polytron, and kept on ice until used.

Incubation Conditions

All incubations were for 60 minutes at 25° C. in 12×75 mm glass tubes containing 1 ml Tris with 5 mg original tissue weight of rat weight of rat striatal membranes, 4 nM [$^3$H]-N-ethyl adenosine-5'-carboxamide ([$^3$H]NECA), 50 nM $N^6$-cyclopentyladenosine (to eliminate $A_1$ receptor binding), 10 mM $MgCl_2$, 0.1 units/ml of adenosine deaminase and 1% dimethylsulfoxide. $N^6$-Cyclopentyladenosine was dissolved at 10 mM in 0.02N HCl and diluted in Tris. Stock solutions and dilutions of $N^6$-cyclopentyladenosine could be stored at $-20°$ C. for several months. Test compounds were dissolved at 10 mM in dimethylsulfoxide on the same day as the experiment, and diluted in dimethylsulfoxide to 100× the final incubation concentration. Control incubations received an equal volume (10 $\mu$l) of dimethylsulfoxide; the resulting concentration of dimethylsulfoxide had no effect on binding. [$^3$H]NECA was diluted to 40 nM in Tris. The membrane suspension (5 mg/0.79 ml) contained sufficient $MgCl_2$ and adenosine deaminase to give 10 mM and 0.1 units/ml, respectively, final concentration in the incubation. For test compounds with $IC_{50}$ values less than 1 $\mu$M, the order of additions was test compound (10 $\mu$l), $N^6$-cyclopentyladenosine (100 $\mu$l), [$^3$H]NECA (100 $\mu$l), and membranes (0.79 ml). For test compounds with $IC_{50}$ values greater than 1 $\mu$M and limited water solubility, the order of additions (same volumes) was test compound, membranes, $N^6$-cyclopentyladenosine, and [$^3$H]NECA. After all additions, the rack of tubes was vortexed, and the tubes were then incubated for 60 min at 25° C. in a shaking water bath. The rack of tubes was vortexed an additional time halfway through the incubation.

Incubations were terminated by filtration through 2.4 cm GF/B filters under reduced pressure. Each tube was filtered as follows: the contents of the tube were poured onto the filter, 4 ml of ice-cold Tris were added to the tube and the contents poured onto the filter, and the filter was washed twice with 4 ml of ice-cold Tris. The filtration was complete in about 12 seconds. Filters were put in scintillation vials, 8 ml of Formula 947 scintillation fluid added, and the vials left overnight, shaken, and counted in a liquid scintillation counter at 40% efficiency.

Data Analysis

Nonspecific binding was defined as binding in the presence of 100 $\mu$M $N^6$-cyclopentyladenosine, and specific binding was defined as total binding minus nonspecific binding. The $IC_{50}$ was calculated by weighted nonlinear least squares curve-fitting to the mass-action equation.

$$Y = T - S \cdot \frac{D}{D + K}$$

where
Y is cpm bound
T is cpm total binding without drug
S is cpm specific binding without drug
D is the concentration of drug and
K is the $IC_{50}$ of the drug Weighting factors were calculated under the assumption that the standard deviation was proportional to the predicted value of Y. Nonspecific binding was treated as a very large (infinite) concentration of drug in the computer analysis.

The $IC_{50}$ values (nM) for adenosine $A_1$ and $A_2$ receptor affinity are reported in the table.

| Example | Receptor Binding | |
|---|---|---|
| | RBA-1 (nM) | RBA-2 (nM) |
| 1 | 7.7 | 343 |
| 2 | 12 | 303 |
| 3 | 4.5 | 549 |
| 4 | 4.3 | 413 |

ANTIPSYCHOTIC EVALUATION

The compounds of the invention are new chemical substances which are useful as pharmaceutical agents for the treatment of psychoses. The antipsychotic activity of representative compounds of the invention was established by the Mouse Activity and Screen Test Procedure (MAST) described below.

Animals

Nine unfasted Swiss-Webster male mice weighing 20–30 g are equally divided into three groups for each drug dose to be tested. That is, data for each dose level was generated by three separate groups of three mice each.

Drugs

A minimum of three dose levels (10, 30, and 100 mg/kg) are tested for each drug. Treatments are administered intraperitoneally one hour prior to testing. All dosages are calculated as parent compound and given in volumes of 10 ml/kg. Compounds are dissolved or suspended in 0.2% Methocel. Control animals are injected with Methocel.

Testing: A two part testing procedure is started one hour postinjection. First, the screen test (ST) is performed (see *Pharmac. Biochem. Behav.* 6, 351–353, 1977). Briefly this test consists of placing mice on individual wire screens which are then rotated 180 degrees at the start of a 60 second observation period. The number of mice falling off the inverted screen is recorded.

Immediately following the screen test, the final phase of testing is initiated by placing each group of three mice in one actophotometer (*Life Sciences*, 22, 1067–1076, 1978). The actophotometer consists of a cylindrical chamber whose center is occupied by another cylinder which contains the illumination for six photocells located on the perimeter of the chamber. Six light-beam interruptions equal one count. Locomotor activity is recorded by computer at ten minute intervals for 60 minutes.

Data: The data obtained from the screen test are expressed as percent of mice falling off the screen. Data derived from locomotor activity of drug treated mice are compared to the activity of vehicle treated animals and are expressed as percent inhibition of spontaneous locomotion. All percentages reported for inhibition of locomotion (LI) are based upon data accumulated for one hour. Both phases of testing are graded: A=60–100%; C=31–59%; and N=0–30%. An overall dose rating is obtained by the following criteria:

| Inhibition of Locomotion Rating | with | Screen Test Dose Failure Rating | = | Rating |
|---|---|---|---|---|
| A | — | N or C | = | A |
| A | — | A | = | C |
| C | — | N or C | = | C |
|   |   | All other combinations | = | N |

LAD refers to the lowest dose at which an A rating is achieved. Compounds which exhibit an overall dose rating of A at a dose of 100 milligrams/kilogram or less are considered active. Utilizing this procedure, an overall dose rating of A was obtained for the noted compound at the indicated dose. The compounds are identified in the Examples.

| Antipsychotic Evaluation | | | |
|---|---|---|---|
| Example | Dose mg/kg | Inhibition of Mouse Locomotion Activity | Screen Test Failure |
| 1 | (IP) 3 | 23% | 0% |
|   | 10 | 48% | 11% |
|   | 30 | 92% | 11% |
|   | (PO) 3 | 12% | 17% |
|   | 10 | 42% | 0% |
|   | 30 | 84% | 44% |
| 2 | (IP) 3 | 21% | 0% |
|   | 10 | 30% | 11% |
|   | 30 | 63% | 0% |
| 3 | (IP) 3 | 27% | 0% |
|   | 10 | 54% | 0% |
|   | 30 | 86% | 0% |
| 4 | (IP) 3 | 48% | 0% |
|   | 10 | 63% | 0% |
|   | 30 | 89% | 0% |

ANTIHYPERTENSIVE EVALUATION (AHP3)

The usefulness of the compounds of the present invention as antihypertensive agents is demonstrated by their effectiveness in standard pharmacological test procedures, for example, in causing a significant decrease in mean arterial blood pressure in the conscious rat. This test procedure is described in the following paragraphs.

Method for the Direct Monitoring of Aortic Blood Pressure and Heart Rate from Conscious Rats The continuous monitoring of pulsatile blood pressure (BP) from unrestrained conscious rats surgically equipped with polyethylene cannulas was accomplished by means of a computer assisted data capture scheme (CADCS). The basic elements of the methodology are the cannulation procedure and the CADCS.

Method Cannulation Procedure: Rats were anesthetized with Telazol (1:1 tiletamine HCl and zolazepam HCl); 20–40 mg/kg IM and the descending aorta exposed via a midline incision. Cannulas fabricated from polyethylene tubing were inserted into the aorta via an undersized puncture hole below the renal arteries. The puncture hole was made by a 23 G disposable needle with a section of the aorta clamped off above and below the puncture site. The cannulas, consisting of a PE100 (0.86 mm ID) body and a PE50 (0.58 mm ID) tip, were attached to a trocar, inserted through the psoas muscle, and passed subcutaneously along the midline of the back and externalized between the ears. The cannulas were anchored to the psoas muscle and between the scalulae (3-0 green braided suture). The midline incision was closed in two steps (muscle first, skin second) using continuous over-and over sutures (4-0 chronic). Each rat was then given penicillin 30,000 units subcutaneously (Penicillin G Procaine Sterile Suspension).

The rats were fitted with a harness-spring-swivel assembly designed to protect the cannula and to provide the rat relative freedom of movement. The harnesses were fabricated from nylon hook and loop tape cemented to a metal plate to which spring wires (18-8 stainless steel), were attached to brass swivels. Each polyethylene cannula was channeled through a spring and connected through a swivel to a pressure transducer (Model P23Gb; Statham Instruments; Hato Rey, Puerto Rico) and an infusion pump (Sage model 234-7; Orion Research, Cambridge, Mass.) by means of PE100 tubing. While on test, each rat received a continuous slow infusion of heparinized saline solution (approximately 400 1 or 40 units of heparin per 24 hour period) to prevent clot formation. Additional "flushes" of the cannula with heparinized saline were carried out when the aortic pulse pressure (systolic minus diastolic) was less than 25 mm Hg.

CADCS: The pulsatile blood pressure and heart rate of each of 32 rats was monitored every minute by means of two in-laboratory microcomputers communicating directly with a data concentrator computer. The data were first stored on the data concentrator disk and then transferred to a magnetic tape for analysis and report generation by the main research computer. The overall scheme involved modulating the primary signal from the pressure transducer, generating the primary data set of the one-minute values for systolic, diastolic, and mean blood pressures and heart rate by the in-lab microcomputer and the storage, analysis, and report generation by the main reserach computer.

The transducers were connected to analog signal conditioning modules. The modules provided a regulated excitation voltage for the transducers, amplification as required to interface the microprocessors and an active low pass filter to compensate for the pressure wave form distortion produced by the flexible, fluid filled, narrow cannula. The distortion was 22–26 Hz and this provided a reliable estimate of both systolic and diastolic blood pressure.

The microcomputers (one for each of two groups of 16 rats) were connected to the input components through the module interface units, an analog-to-digital converter for the pressure wave form signal and the digital inputs for the dose and event marker switches. The microcomputer controlled the sequential acquisition of data from the modular interface units through an internal synchronous time-of-day clock/time base generator. Utilizing the time base generator as a reference, the blood pressure values and the marker switch status for each of the 32 stations were sampled every ten msec. The microcomputer processed each blood pressure sample as it was received to produce "running average" values for heart rate, and mean, systolic and diastolic blood pressures.

When tested by the above procedure, compounds of Examples produced the following changes in MAP and heart rate. LAD refers to the lowest dose tested at which a >10% reduction in blood pressure for four consecutive hours is achieved.

| Example Number | mg/kg | | AHP Data Hour | | | | |
|---|---|---|---|---|---|---|---|
| | | | 1 | 3 | 5 | 7 | 9 |
| 1 | 10 | M.A.P. | ↓9% | ↓13% | ↓5% | ↓5% | ↓9% |
| | | HR. | ↑4% | ↓6% | ↑8% | ↑3% | ↑6% |
| 2 | 10 | M.A.P. | ↓11% | ↓13% | ↓12% | ↓11% | ↓12% |
| | | HR. | ↓2% | ↓2% | ↑2% | ↑12% | ↑11% |
| 4 | 10 | M.A.P. | ↓5% | ↓15% | ↓19% | ↓10% | ↓4% |
| | | HR. | ↓3% | ↓11% | ↓23% | ↑6% | ↑11% |

ANALGESIC EVALUATION

Accordingly, the present invention also includes a pharmaceutical composition for treating psychoses, sleep disorders, pain, or hypertension comprising a corresponding antipsychotic, sedative, analgesic, or antihypertensive effective amount of a compound of the formula I as defined above together with a pharmaceutically acceptable carrier.

The present invention further includes a method for treating psychoses, sleep disorders, pain, or hypertension in mammals suffering therefrom comprising administering to such mammals either orally or parenterally a corresponding pharmaceutical composition containing a compound of the formula I as defined above in appropriate unit dosage form.

For preparing pharmaceutical compositions from the compounds described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solublizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirrring. The molten homogeneous mixture is then poured into convenient sized molds, allowed to cool and thereby to solidify.

Liquid form preparations include solutions, suspensions, and emulsions. As an example may be mentioned water or water propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 1 mg to 500 mg preferably to 5 to 100 mg according to the particular application and the potency of the active ingredient. The compositions can, if desired, also contain other compatible therapeutic agents.

In therapeutic use as described above, the mammalian dosage range for a 70 kg subject is from 0.1 to 150 mg/kg of body weight per day or preferably 1 to 50 mg/kg of body weight per day. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

The following Examples further illustrate the invention.

EXAMPLE 1

N-[2-(6-methoxybenzo[b]thien-3-yl)ethyl]adenosine

6-Chloropurine riboside (1.7 g, 6 mmol) was added, at once, to a solution of the 2[3-(6-methoxybenzo[b]-thienyl)]ethylamine (CAS Number 14679-07-3) (1.9 g, 9.1 mmol) and triethylamine (1.1 g, 11 mmol) in ethanol (200 ml). This solution was stirred at reflux 48 hours. The solution cooled to room temperature to precipitate. The solid collected by filtration and then washed with ethanol (100 ml). The solid dried for four hours at 65° C. in vacuo: yield 2.4 g (89%), mp 177°-178° C.

Analysis ($C_{21}H_{23}N_5O_5S \cdot H_2O$):
Calc.: C=53.04, H=5.30, N=14.73, S=6.74.
Found: C=53.32, H=5.32, N=14.53, S=6.62.

EXAMPLE 2

N-[2-(benzo[b]thien-3-yl)ethyl]adenosine

The title compound was prepared as in Example 1 using 6-chloropurine riboside (1.15 g, 4 mmol), 2-(3-benzo[b]thienyl)ethylamine.HCl (CAS Number 148585-66-1) (1.0 g, 4.6 mmol), and triethylamine (1.1 g, 11 mmol); yield 1.5 g (88%), mp 173°-174° C.

Analysis ($C_{20}H_{21}N_5O_4S$):
Calc.: C=56.19, H=4.95, N=16.38, S=7.50.
Found: C=56.31, H=4.97; N=16.09, S=7.28.

EXAMPLE 3

N-[2-(5-chlorobenzo[b]thien-3-yl)ethyl]adenosine

The title compound was prepared as in Example 1 using 6-chloropurine riboside (2.1 g, 7.5 mmol), 2-[3-(chlorobenzo[b]thienyl)]ethyl amine.HCl (CAS Number 23799-77-1) (2.5 g, 10 mmol), and triethyl amine (2.0 g, 20 mmol); yield 2.1 g (60%); mp 167°-169° C.

Analysis ($C_{20}H_{20}ClN_5O_7S - 0.8$ EtOH):
Calc.: C=52.01, H=5.00, N=14.06.
Found: C=52.07, H=4.83, N=14.04.

EXAMPLE 4

N-[2-(5-methylbenzo[b]thien-3-yl)ethyl]adenosine

The title compound was prepared as in Example 1 using 6-chloropurine riboside (1.4 g, 5 mmol), 2-[3-(5-methylbenzo[b]thienyl)]ethyl amine (1.5 g, 6.6 mmol),
and triethylamine (1.2 g, 12 mmol); yield 1.7 g (77%), mp 158°-160° C.

Analysis ($C_{21}H_{23}N_5O_4S$):
Calc.: C=57.13; H=5.25, N=15.86.
Found: C=57.25, H=5.25, N=15.71.

FORMULAE

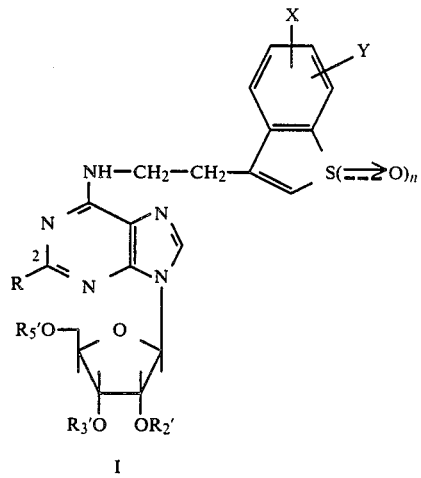

I

SCHEME I

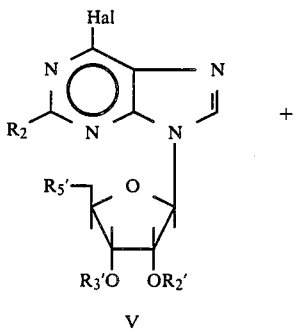

V

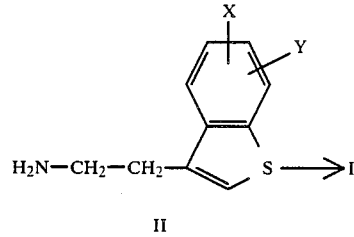 I

II

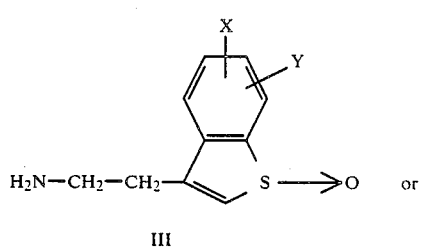 O or

III

I claim:

1. A method of treating immunoinflammation in a mammal suffering therefrom, which comprises administering to such mammals a compound of the formula

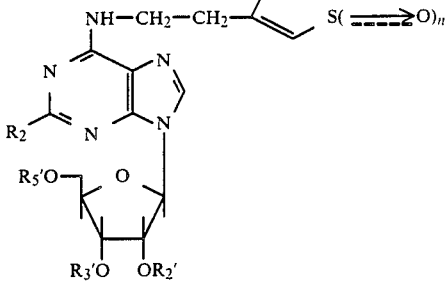

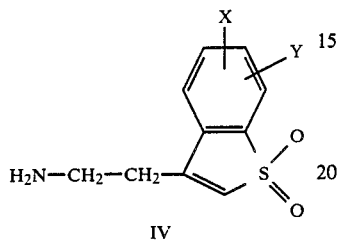

wherein ≡≡≡ is ___ or ═══, n is 0-2, inclusive, X and Y are each independently H, hydroxy, lower alkoxy, lower alkyl, amino, mono-lower alkylamino, di-lower, alkylamino, nitro, or halogen; $R_2$ is H, halogen, or amino; $R_2'$, $R_3'$, and $R_5'$ are independently H, lower alkanoyl, benzoyl, or benzoyl substituted by lower alkyl, lower alkoxy, halogen, or when taken together, $R_2'$ and $R_3'$ may be 2',3'-lower alkylidene; or pharmaceutically acceptable acid addition salts thereof in unit dosage form.

2. A method of claim 1 wherein n is 0.
3. A method of claim 1 wherein n is 1 or 2.
4. A method of claim 2 wherein one of X and Y is not hydrogen or lower alkyl.
5. A method of claim 4 wherein $R_2$ is not hydrogen.
6. A method of claim 4 wherein $R_2'$, $R_3'$, and $R_5'$ are hydrogen.
7. A method of claim 3 wherein n is 1.
8. A method of claim 3 wherein n is 2.
9. A method of claim 2 wherein the embodiment is N-[2-(benzo[b]thien-3-yl)ethyl]adenosine or a pharmaceutically acceptable salt thereof.
10. A method of claim 4 wherein the embodiment is N-[2-(6-methoxybenzo[b]thien-3-yl) ethyl]adenosine or a pharmaceutically acceptable salt thereof.
11. A method of claim 4 wherein the embodiment is N-[2-(5-chlorobenzo[b]thien-3-yl) ethyl]adenosine or a pharmaceutically acceptable salt thereof.
12. A method of claim 4 wherein the embodiment is N-[2-(5-methylbenzo[b]thien-3-yl) ethyl]adenosine or a pharmaceutically acceptable salt thereof.

* * * * *